(12) United States Patent
Dougherty et al.

(10) Patent No.: US 8,247,167 B2
(45) Date of Patent: Aug. 21, 2012

(54) HIV-1 LATENCY MODEL FOR HIGH THROUGHPUT SCREENING

(75) Inventors: Joseph P. Dougherty, Milford, NJ (US); Sofiya Micheva-Viteva, Los Alamos, NM (US); Stuart W. Peltz, Califon, NJ (US); Yacov Ron, East Brunswick, NJ (US); Annmarie L. Pacchia, Buffalo, NY (US)

(73) Assignee: University of Medicine and Dentistry of New Jersey, New Brunswick, MA (US)

( * ) Notice: Subject to any disclaimer, the term of this patent is extended or adjusted under 35 U.S.C. 154(b) by 395 days.

(21) Appl. No.: 12/096,245

(22) PCT Filed: Nov. 27, 2006

(86) PCT No.: PCT/US2006/045483
§ 371 (c)(1),
(2), (4) Date: Mar. 11, 2009

(87) PCT Pub. No.: WO2007/067386
PCT Pub. Date: Jun. 14, 2007

(65) Prior Publication Data
US 2009/0305227 A1    Dec. 10, 2009

Related U.S. Application Data

(60) Provisional application No. 60/742,241, filed on Dec. 5, 2005.

(51) Int. Cl.
*C12N 7/01* (2006.01)
*C12N 15/867* (2006.01)

(52) U.S. Cl. ......................................... 435/5; 435/235.1
(58) Field of Classification Search .................. None
See application file for complete search history.

(56) References Cited

U.S. PATENT DOCUMENTS

| 2001/0039007 A1* | 11/2001 | Hallowitz et al. ................. 435/5 |
| 2003/0013078 A1 | 1/2003 | Blair et al. |
| 2003/0157693 A1 | 8/2003 | Verdin et al. |

FOREIGN PATENT DOCUMENTS

| WO | 2006029029 A2 | 3/2006 |
| WO | WO 2006029029 * | 3/2006 |

OTHER PUBLICATIONS

Cannon, et al. Analysis of Tat Function in Human Immunodeficiency Virus Type 1-Infected Low Level Expression Cell Lines U1 and ACH-1. J. Virol. 1994; 68(3): 1993-1997.*
Mace, et al. Retroviral Envelope Protein Fusions to Secreted and Membrane Markers. Virology. 1992; 188(2): 869-74. Abstract Only.*

(Continued)

*Primary Examiner* — Zachariah Lucas
*Assistant Examiner* — Stuart W Snyder
(74) *Attorney, Agent, or Firm* — Hoffman & Baron, LLP

(57) ABSTRACT

Isolated, latently infected T cell lines are provided that can be utilized in high throughput screening to discover compounds capable of activating HIV-I. The T cell lines harbor a latent HIV-I derived vector pro virus, which upon activation expresses a marker for late viral gene expression due to the insertion of the marker gene in the position of HIV-I envelope.

4 Claims, 8 Drawing Sheets

A    NLE-S-G

B

OTHER PUBLICATIONS

Cannon, et al. Analysis of Tat Function in Human Immunodeficiency Virus Type-1-infected Low-Level-Expression Cell Lines U1 and ACH-2. J. Virol. 1994; 68(3): 1993-1997.*

Perrin-Tricaud, et al. Tagging the Human Immunodeficiency Virus Gag Protein with Green Fluorescent Protein. Virology. 1999; 255(1): 20-25.*

"Data Sheet", Catalog No. 349, NIH AIDS Research & Reference Reagent Program, revised Oct. 8, 2010, downloaded from the web Sep. 8, 2011.*

Perez-Caballero, et al. Human Immunodeficiency Virus Type 1 Matrix Inhibits and Confers Cooperativity on Gag Precursor-Membrane Interactions. Journal of Virology. 2004; 78(17): 9560-9563.*

Ou and Silver. Efficient trapping of HIV-1 envelope protein by hetero-oligomerization with an N-helix chimera. Retrovirology 2005, 2:51.*

Siekevitz, et al., Activation of the IIIV-I LTR by T Cell Mitogens and the Trans-Activator Protein of HTLV-I. Science. 1987; 238:1575-1578.*

Perkins, et al., A cooperative interaction between NF-xB and Sp1 is required for HIV -1 enhancer activation. The EMBO Journal. 1993; 12(9): 3551-3558.*

Griffin, et al. Activation of HIV gene expression during monocyte differentiation by induction of NF•KB. Nature. 1989; 339: 70-73.*

Cannon et al., "Analysis of Tat Function in Human Immunodeficiency Virus Type 1-Infected Low-Level-Expression Cell Lines U1 and ACH-2", Journal of Virology, vol. 68, No. 3, Mar. 1994, pp. 1993-1997.

Kutsch et al., "Direct and Quantitative Single-Cell Analysis of Human Immunodeficiency Virus Type 1 Reactivation from Latency", Journal of Virology, vol. 76, No. 17, Sep. 2002, pp. 8776-8786.

Micheva-Viteva et al., "Human Immonodeficiency Virus Type 1 Latency Model for High-Throughput Screening", Antimicrobial Agents and Chemotherapy, vol. 49, No. 12, Dec. 2005, pp. 5185-5188.

Munier et al., "Characterization of two candidate genes, NCoA3 and IRF8, potentially involved in the control of HIV-1 latency", Retrovirology, Biomed Central Ltd., London, GB, vol. 2, No. 1, Nov. 2005, p. 73.

Page et al., "Use of a Green Fluorescent Protein as a Marker for Human Immunodeficiency Virus Type 1 Infection", AIDS Research and Human Retroviruses, vol. 13, No. 13, Jan. 1997, pp. 1077-1081.

International Search Report for PCT/US06/45483 dated Jun. 5, 2007.

Supplementary European Search Report for EP 06844574 / PCT/US/2006/045483 dated Apr. 22, 2009.

* cited by examiner

HIV-1 LATENCY MODEL FOR HIGH THROUGHPUT SCREENING

CROSS-REFERENCE TO RELATED APPLICATIONS

This application claims the benefit of U.S. Provisional Application No. 60/742,241, filed Dec. 5, 2005, the contents of which are incorporated herein by reference in their entirety.

FIELD OF THE INVENTION

This application relates to a novel HIV-1 latency model that can be used for high throughput screening to identify novel small molecules that can be employed to eradicate latent virus from infected individuals.

BACKGROUND OF THE INVENTION

The advent of highly active antiretroviral therapy (HAART), which involves the use of three or more antiretroviral drugs, has led to a significant improvement in the care and survival of patients infected with HIV-1. In patients not infected with resistant strains of the virus, HAART typically results in a dramatic decrease in viral load often from levels of 10,000-100,000 RNA copies/ml of plasma to less than 50 copies/ml (3).

Given the dramatic effects of HAART, it was proposed that complete elimination of the virus might be possible within 2 to 3 years (36). However, even after long-term suppression of viral replication with HAART, the virus rapidly rebounds after therapy is discontinued (7,12). A key contributor to viral rebound appears to be a reservoir of latently infected cells, including CD4[+] memory T cells. The half-life of the latently infected population is quite long, and it is estimated that it would take over 60 years of HAART to eliminate this population (15). Therefore, life-long HAART would be required to control infection in patients.

Retroviruses, including HIV-1, are RNA viruses that replicate through a DNA intermediate and integrate very efficiently into the genome of an infected cell forming a provirus. Once the provirus is formed, it is maintained in the genome of the infected cell and transferred to daughter cells in the same fashion as any other genetic element within the cellular genome. Thus, the virus has the potential to persist if it infects long-lived cells such as memory T cells. It has been known since 1986 (17) that HIV-1 can establish a latent infection in culture. It was found that a human T cell line infected with replication-competent virus could develop a latent infection in which the provirus was dormant but could be reactivated upon stimulation. Since then it has been established that a number of cytokines including tumor necrosis factor (TNF)-α and even a small molecule such as the phorbol ester, phorbol 12-myristate 13-acetate (PMA) can reactivate latent proviruses (30).

The role that latency is playing in preventing clearance of the virus infection has become evident in recent years. Patients that had been successfully treated with HAART in which viral RNA was maintained at levels below 50 copies/ml in the plasma for years, experienced rapid virus rebound upon withdrawal of therapy (7,12). Moreover, it was found that after T cell activation, virus could be isolated from CD4[+] T cells taken from these patients making it clear that to eradicate the virus it will be necessary to eliminate the latently infected cells (10,16,19,45).

There have been attempts to flush the latent virus from infected individuals by non-specific activation of T cells to "turn on" latent proviruses. As part of this approach, the patients remain on HAART to prevent new infections, and the infected cells from which the latent proviruses are activated should die due to cytotoxic effects of viral expression and/or because of targeting by the immune system which can recognize the cells once they begin to express the viral proteins (3). One approach employed the combination of a monoclonal antibody against CD3 on T cells plus IL-2 to activate T cells and consequently the latent proviruses (37). Other approaches have used IL-2 with or without additional cytokines (8,13,31,41). To date, none of these protocols have been successful, and at least some of them have toxic side effects, which is not surprising considering the massive T cell activation that occurs. One plausible reason for the lack of latent provirus clearance could be due to the inability of the therapeutic regime to reach all of the latent reservoirs.

A potentially fruitful approach to eliminating virus infection would be to identify small molecules with pharmacological properties that allow these molecules to reach hard to access latent reservoirs in order to activate latent proviruses. There is precedent for a small molecule that can activate latent HIV-1 proviruses, since it was found that the tumor-promoting phorbol ester PMA could stimulate latent virus. This has led to recent studies with a non-tumor promoting phorbol ester, prostratin, which has also been found to be able to activate latent virus leading to the hypothesis that prostratin can be employed to help eradicate latent infection (2729). However, it is not presently known whether prostratin has the appropriate pharmacological properties to enable total clearance of latent virus nor is it certain that only one drug will be enough for latent virus elimination. Moreover, it was recently reported that prostratin displayed significant cytotoxicity putting into question its use in a clinical setting (43).

Thus, there is a need in the art for further strategies to discover new drugs capable of activating latent HIV-1. Preferably, there is a need for a cell-based assay that can be utilized in high throughput screening (HTS) to discover novel compounds capable of activating latent HIV-1.

SUMMARY OF THE INVENTION

The present invention solves a need in the art by providing an isolated, latently infected T cell line that can be utilized in high throughput screening to discover compounds capable of activating HIV-1.

In particular, the present invention provides an isolated T cell line harboring a latent HIV-1 derived vector provirus, which upon activation of the provirus expresses a secretable marker for late viral gene expression, the gene for said marker being inserted in the position of HIV-1 envelope.

Further provided is an in vitro cell-based method of identifying compounds capable of activating latent HIV-1. The method includes providing an isolated T cell line harboring a latent HIV-1 derived vector provirus, which upon activation of the provirus expresses a secretable marker for late viral gene expression due to the insertion of the marker gene in the position of HIV-1 envelope; and providing a candidate compound. The method further includes combining T cells from the T cell line with the candidate compound; and monitoring proviral activation in the presence of the candidate compound as compared to in the absence of the candidate compound to determine if the compound is capable of activating latent HIV-1.

DETAILED DESCRIPTION OF THE INVENTION

Figure 1:
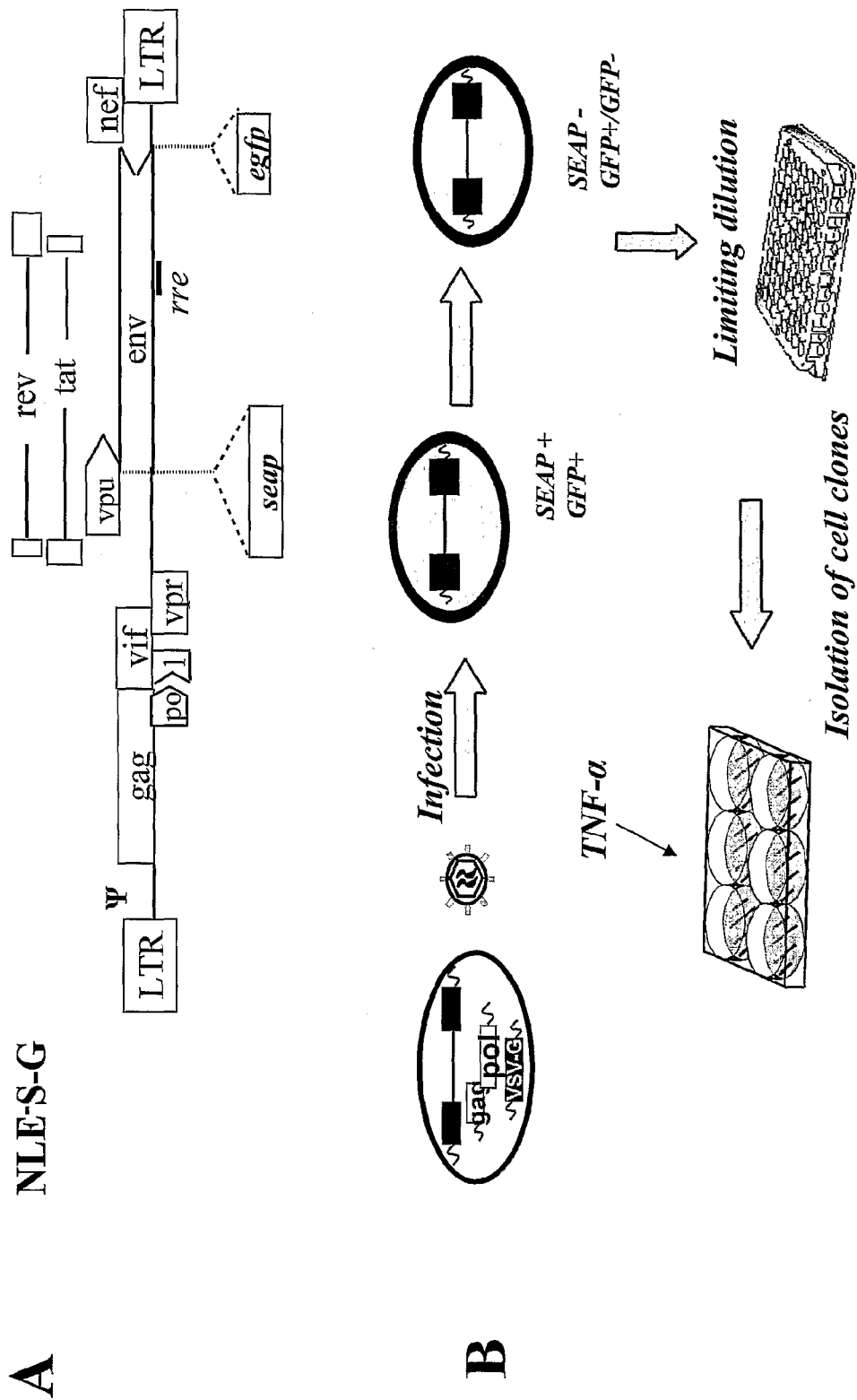
FIG. 1. Schematic diagram of the HIV-I transducing vector and outline of the protocol for establishing latent clonal cell lines. (A) NLE⁻S-G is a lentiviral vector that contains all the cis-acting elements required for replication as well as two reporter genes: seap in the env position and egfp positioned 5' to the start of codon of nef. Abbreviations: LTR, long terminal repeats; rre, Rev response element; ψ, packaging signal; seap, secreted alkaline phosphatase; egfp, enhanced green fluorescent protein. Arrowheads represent partial deletions of viral sequence. (B) Vector virus was propagated in 293T cells by transient co-transfection with plasmids expressing pol and VSV-G-env (plasmids pCMVΔR8.2 and pMD.G, respectively). Most of the viral cis-acting elements in pCMVΔR8.2 were deleted to prevent the likelihood of producing replication-competent virus. Vector virus was then used to infect SupT1 cells. Three or four weeks post-infection cell clones were isolated by limiting dilution. Only clones producing low or undetectable levels of seap that could be reactivated with 100 ng/ml TNF-α were used to establish cell lines.

As described above, highly active antiretroviral therapy (HAART) has had an important impact upon morbidity and mortality from AIDS. Although HAART results in a remarkable suppression of HIV-1 replication in infected patients, it does not provide for elimination of the virus even after years of suppressive therapy. Complete viral clearance cannot be achieved due to the presence of latently infected cells in patients, which upon withdrawal of HAART, contribute to viral rebound. Attempts at eradicating latently infected cells by activating them with cytokines and lymphokines has not met with success probably owing both to the inability of this treatment to reach all of the latent viral reservoirs and to the toxicity of the regimen. Small molecules with pharmacological properties that allow them to reach all viral reservoirs and activate latent HIV-1 proviruses could very well result in clearance of HIV-1 infections when used in combination with HAART.

The present invention is directed, at least in part, to the development of a latently infected T cell line that can be used for high throughput screening (HTS) to identify small molecules that can be employed to eradicate latent virus from infected individuals. In some embodiments, an isolated T cell line of the present invention harbors a latent HIV-1 derived vector provirus, which upon activation expresses a secretable enzyme, such as secretable alkaline phosphatase (SEAP), as a marker for late viral gene expression due to insertion of the marker gene in the position of HIV-1 envelope.

In some embodiments, the secretable marker is capable of being detected using chemiluminescence. For example, SEAP production can be monitored by employing a sensitive chemiluminescent reaction.

In some further embodiments, the T cell lines of the present invention harbor a latent provirus capable of being activated by stimuli selected from TNF-α, PMA, valporic acid and combinations thereof. For example, the isolated T cell line of the present invention harbors a latent provirus that was activated using various stimuli previously shown to induce latent HIV-1, including TNF-α, PMA, and valporic acid. A reproducible signal was detected in a small well format. The excellent reliability of the assay was characterized by a Z' factor with values ranging between 0.55 and 0.80.

In some embodiments, the latent provirus in the cell line is replication-incompetent. For example, because the latent provirus was derived from a defective HIV-1 vector, it allows HTS to be performed safely since replication-competent virus would not be produced during screening. Thus, this system provides a safe, sensitive, and reliable assay for novel drug discovery aimed at eradication of HIV-1 infection.

In some embodiments, the T cell lines of the present invention harbor latent HIV-1 vector proviruses containing two marker genes that can be used for antiviral drug discovery, as well as for studying the mechanism of HIV-1 latency.

In some embodiments, seap marker makes the system amenable to high throughput screening and given its placement in the genome reflects activation of viral late gene expression.

In some other embodiments, the latent provirus expresses a marker for viral early gene expression at the single cell level. For example, in some embodiments, a gene encoding a fluorescent protein, such as the egfp gene, allows monitoring activation of the viral early gene expression at the single cell level. In addition, it provides a different marker in the system that can be used as a rapid secondary screen to control for artifacts that may arise when monitoring seap expression, such as a particular compound yielding a false positive. Fluorescence from a fluorescent protein may be detected using fluorescent microscopy, flow cytometry or combinations thereof, for example.

Furthermore, in some embodiments, the latent provirus contains an intact HIV-1 gag gene, thereby allowing the use of Gag expression as a further marker of viral gene expression. For example, in some embodiments, Gag expression may be used as an additional marker for rapid secondary screening of putative "hit" compounds.

Another important characteristic of the latency model described here is that it yields excellent reliability in a small well format as reflected by the Z' scores obtained in assays with one of the cell lines, which is important for successful HTS. Moreover, since the vector provirus is replication-incompetent, it provides a level of safety needed when assaying a large number of samples as would be the case for HTS using robotic screening.

It is noteworthy that the cell lines have been cultured extensively for at least six months and still retain the same characteristics described above. This indicates that the cell lines are quite stable over time.

Despite the interesting research done on the mechanism of HIV-1 latency, there is still no clear understanding about how latency is established and maintained. It is apparent that latency is characterized by a state of relative transcriptional inactivity. This is the case both in vivo in quiescent CD4$^+$ memory T cells (22,32) and in vitro in previously established models of HIV-1 latency (30,39). Another common theme to latency in vivo and in vitro is that various cytokines as well as other activators such as phorbol esters can activate latent virus (18,28,30,37,39,42). These attributes are reflected in the cell lines of the present invention in which gene expression is low until activated with the appropriate stimulus.

The in vitro cell-based model provided by the present invention reproduces the major molecular characteristics of latency observed in vivo. These similarities lend confidence that the in vitro cell model is useful for identifying compounds that can activate latent proviruses. Candidate compounds identified using the cell-based methods of the present invention may be further tested for their ability to successfully activate latent proviruses from patient samples.

The in vitro cell-based method of identifying compounds capable of activating latent HIV-1 includes providing an isolated T cell line harboring a latent HIV-1 derived vector provirus, which upon activation of the provirus expresses a marker for late viral gene expression due to the insertion of the marker gene in the position of HIV-1 envelope; and providing a candidate compound. The method further includes combining T cells from the T cell line with the candidate compound; and monitoring proviral activation in the presence of the candidate compound as compared to in the absence of the candidate compound to determine if the compound is capable of activating latent HIV-1.

In some embodiments, the monitoring step further includes combining T cells from the T cell line with a positive control for latent proviral activation; and monitoring proviral activation in the presence of the positive control. For example, the positive control may be a stimuli selected from, but not limited to, the following: tumor necrosis factor (TNF)-α, phorbol 12-myristate 13-acetate (PMA), valporic acid and combinations thereof. In some further embodiments, the method of identifying compounds capable of activating latent HIV-1 may further include determining the ability of a candidate compound to activate latent HIV-1 from patient samples.

The T cell line used in the method of the present invention harbors a latent provirus. The latent provirus contains a gene encoding a secretable marker for late viral gene expression. Upon activation of the latent provirus, the T cells secrete the marker for late viral gene expression. For example, the secretable marker may be a secretable enzyme, such as secretable alkaline phosphatase. In this instance, the monitoring step in the method may include detecting enzymatic activity of the secreted alkaline phosphatase in the presence of an alkaline phosphatase substrate. Examples of suitable chemiluminescent substrates for alkaline phosphatase include CSPD® and CDP-Star®, which are available from Applied Biosystems (Bedford, Mass.). However, the present invention is not limited to these.

The latent provirus in the cells used in the method of the present invention may further contain a marker gene for early viral gene expression. In some embodiments, the expressed marker for early viral gene expression is a fluorescent protein, such as a green fluorescent protein. In this instance, the method of the present invention may further include detecting cell fluorescence by fluorescent microscopy, flow cytometry or combinations thereof.

The latent provirus in the cells employed in the method of the present invention preferably contain an intact HIV-1 Gag gene. This allows the use of Gag expression by the cells as an additional marker for rapid secondary screening of putative "hit" compounds. Therefore, in some embodiments, the inventive method includes detecting HIV-1 Gag expression.

Figure 3:
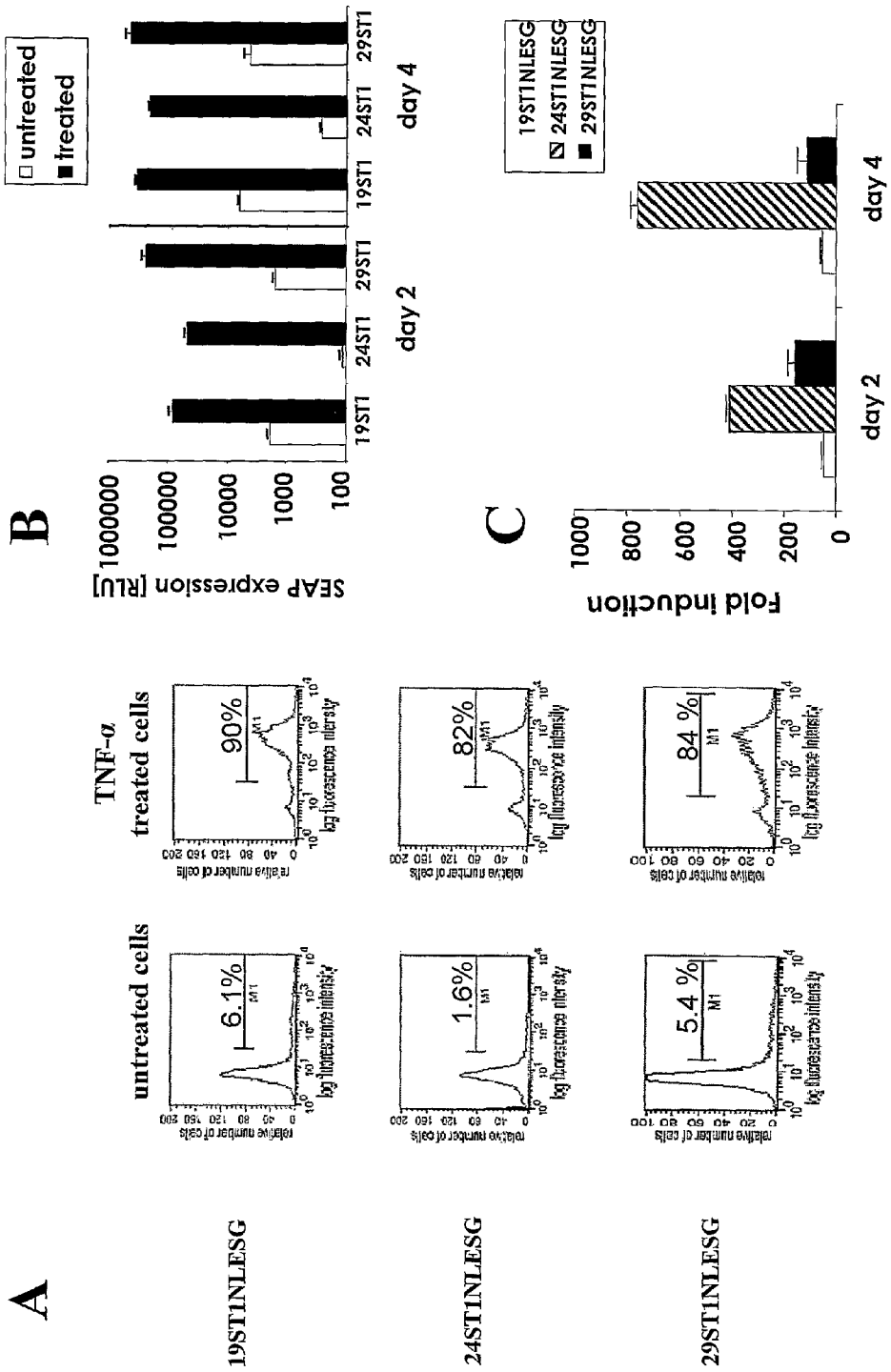
FIG. 3. Reactivation of early and late viral gene expression in three clonal cell lines by TNF-α. (A) 19ST1NLESG, 24ST1NLESG, and 29ST1NLESG cells ($10^6$/ml) were exposed to TNF-α (50 ng/ml) and four days after gfp expressing cells were analyzed by flow cytometry. The left panels show the histograms of unstimulated cells, and the right panels represent the histogram analysis of TNF-α (50 ng/ml) stimulated cells. Numbers show the percentages of gfp positive cells. (B) SEAP in the cultured media of untreated and TNF-α (50 ng/ml) stimulated 19ST1NLESG, 24ST1NLESG, 29ST1NLESG cells two and four days post plating. (C) Fold induction of SEAP expression in 19ST1NLESG, 24ST1NLESG, and 29ST1NLESG cells ($10^6$/ml) after stimulation with TNF-α (50 ng/ml). Readings were taken on the second and fourth days post activation. Results shown are the means and standard deviations of one of three representative experiments.

Although the background levels of gene expression are low for the cell lines of the present invention, some expression is still detectable even for the 24ST1NLESG line with the lowest background levels of expression (FIG. 3). This has also been noted in other in vitro models of latency (30,39) and it has also been observed in vivo. For example, when viral mRNA levels are examined in highly purified CD4$^+$ memory cells from patients successfully undergoing HAART suppressive therapy, low but detectable levels of viral RNA can be found in the absence of virus production (32). Once activated these cells are capable of producing virus (5,9,19,24). Thus, it is not unexpected that some background expression from the latent provirus would be found in the model system of the present invention. Moreover, the background expression is not the same for the three cell lines depicted in FIG. 3.

One potential influence upon the background level of expression is the site of integration. Since the proviruses are integrated in different positions in the genome (FIG. 5), the local site of integration can influence expression from the provirus and could, at least in part, account for the different levels of background expression (23,26,44).

Another characteristic of the cell clones described here was the apparent variegated expression of egfp within each clonal population (FIG. 3A). Upon activation with TNF-α, the number of cells expressing egfp was quite high ranging from 82% to 90% of the cells by day 4 post-activation. However, a relatively small fraction of the cells were not activated (FIG. 3A). This variegated expression indicates that there might be some level of epigenetic regulation of expression. This might be related to disparate responses of cells to TNF-α stimulation in different phases of the cell cycle (39) or due to heterochromatic packaging (14). This suggests that it may be necessary to administer a therapeutic activator repeatedly to patients or that a cocktail of activators may be required to "flush" the virus from all of its latent reservoirs.

As described herein, additional cell clones were isolated with higher levels of background expression, yet with excellent levels of inducibility. Initial screening for compounds that activate latent virus would be done employing the 24ST1NLESG cell line given its low background and high degree of inducibility. However, the other cell clones can be utilized for secondary screening. Any promising compound identified by HTS would be anticipated to also be able to activate latent proviruses integrated in different locations. The other cell clones provide a rapid and safe secondary screen that would be able to quickly rule out artifacts such as effects dependent upon the specific site of integration.

The present invention provides the first HIV-1 latency model that has been developed that can be used for high throughput screening to identify novel small molecules that can be employed to eradicate latent virus from infected individuals.

Vector System

The present inventors have developed a cell-based assay that can be used in HTS to discover novel compounds that can activate latent HIV-1 proviruses. The marker gene that is being utilized in this system is the secretable alkaline phosphatase (seap) gene, a truncated form of placental alkaline phosphatase lacking the membrane anchor so that it is secreted (2). It provides a very sensitive chemiluminescent assay when used in conjunction with the alkaline phosphatase substrate CSPD and as such is amenable to HTS. It has been shown that as little as $10^{-13}$ g of placental alkaline phosphatase can be detected (4,46). Other advantages are (2,46): (1) SEAP is heat stable and resistant to the alkaline phosphatase inhibitor L-homoarginine, which allows endogenous alkaline phosphatase (AP) activity to be eliminated via pretreatment at 65° C. with the inhibitor; (2) because it is secreted, there is no necessity for preparation of cell lysates; (3) the chemiluminescence assay has a linear dynamic range of over four orders of magnitude, which helps control experimental parameters to obtain readouts in the linear range allowing valid comparisons among the different samples, and (4) the signal reaches a maximum at approximately 10 minutes after the reaction and remains stable for at least an hour which augments the reproducibility of the assay.

Since a hallmark of active replication is production of the HIV-1 late proteins including the viral envelope polyprotein (Env), the seap gene was inserted in the env position to serve as an indicator of late gene expression (FIG. 1). Disruption of the env gene by insertion of seap in place of the env start codon, imparts a level of safety to the system by preventing production of the essential Env polyprotein. However, in order to include an additional level of safety to prevent production of replication-competent virus, 2.5 kbp of the pol gene was also deleted, since it has not been reported to contribute to the establishment of latency but is essential for replication (FIG. 1).

In addition to the seap gene, the enhanced green fluorescent protein (egfp) reporter gene was inserted 5' to the nef start codon such that it should be expressed from the multiply spliced nef mRNA (FIG. 1) (38,40). The egfp gene was included in the system to provide a marker that would allow monitoring of infection by fluorescent microscopy and flow cytometry as well as providing a marker for subsequent isolation of latently infected cell clones.

Vector Characterization

Figure 2:
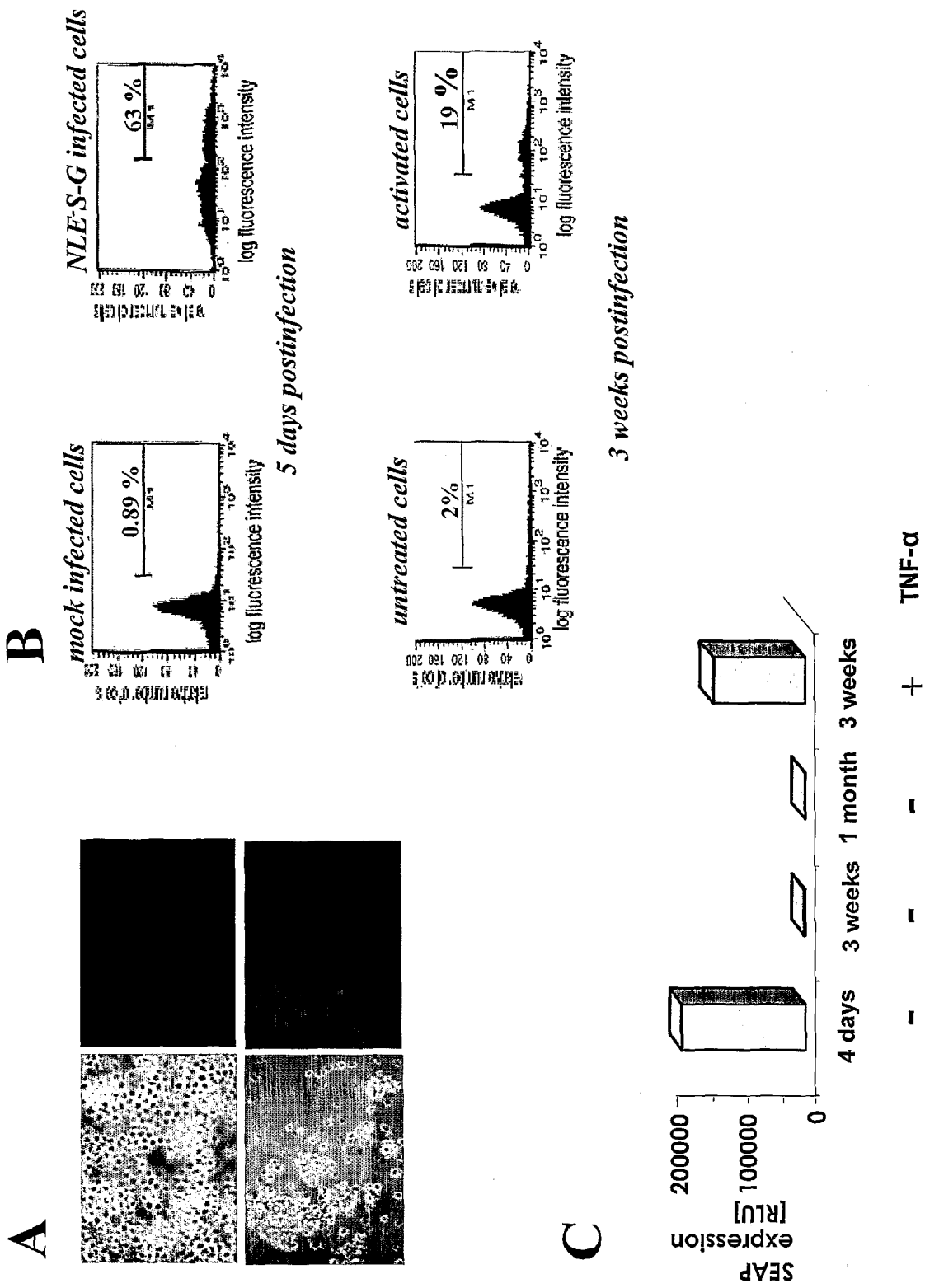
FIG. 2. Infection of SupT1 cells by NLE⁻S-G vector virus. (A) The upper panels depict uninfected SupT1 cells. The lower panels show SupT1 cells that have been infected with NLE-S-G virus. The phase contrast (left panels) and fluorescence microscopy (right panels) images were captured five days post-infection. (B) Flow cytometric analysis of SupT1 cells either mock infected or infected with NLE⁻S-G analyzed at day five post-infection or three weeks post-infection. Mock infection was performed using a lentiviral vector that does not carry seap or egfp. Three weeks post infection mass population of unsorted NLE⁻S-G infected SupT1 cells ($10^6$ cells/ml) were stimulated with TNF-α (100 ng/ml). Cells were analyzed forty-eight hours after exposure. Numbers represent the percentages of gfp positive cells. (C) SEAP activity in the conditioned media from NLE⁻S-G infected unsorted SupT1 cells ($10^6$ cells/ml) four days, three weeks and one month post-infection. Three weeks post-infection, a sample ($10^6$ cells/ml) of a mass population of NLE⁻S-G infected SupT1 cells was treated with TNF-α (100 ng/ml) and analyzed four days post activation. RLU, relative light units.

In order to propagate vector virus, the vector was cotransfected into 293T cells along with plasmids pCMVΔR 8.2 and pMD.G (33) to complement the pol and env defects, respectively. It is noteworthy that pMD.G expresses the vesicular stomatitis G protein which allows the production of pseudotyped vector virus that can be readily concentrated by ultracentrifugation (6,35). Vector virus supernatants were collected, concentrated, and used to infect the human lymphocyte based cell line SupT1 via spinoculation (Examples) (34). A surprising observation was made when SupT1 cells were transduced with the vector pNLE S-G containing an intact vpu start codon. Although vector virus could effectively transduce the SupT1 cells as evidenced by EGFP expression in the infected cells, SEAP was not expressed (data not shown). HIV-1 env is translated from a vpu-env bicistronic mRNA (20,38). It was believed that translation initiation of env occurs due to a leaky scanning mechanism (20). It was possible that due to the insertion of SEAP, leaky scanning was inhibited. To address this problem, the start codon of vpu was destroyed to allow SEAP expression from a monocistronic RNA. The resultant vector virus could efficiently infect SupT1 cells as well as express significant levels of SEAP after 4 days post-infection (FIG. 2).

The infected mass population of cells was next tested for its ability to establish a latent infection. The infected mass population of SupT1 cells was maintained in culture for one month. By week three, flow cytometry indicated that most of the infected cells had died and/or reverted to a latent phenotype as denoted by the reduction of the GFP positive cells declining from 63% on day 5 to 2% 3 weeks post-infection (FIG. 2B). This was also reflected in the reduction of SEAP expression by the third week (FIG. 2C). It was shown in previous studies that tumor necrosis factor (TNF)-α could activate HIV-1 virus production from latently infected cell lines (30). The mass population was treated with TNF-α, and it was found that there was a significant increase in the number of GFP-positive cells to 19% as well as a 400-fold increase in SEAP activity (FIGS. 2B and C). These results clearly indicated that the vector could form a latent infection and activation could be monitored by SEAP expression.

Isolation and Characterization of Latently Infected Cell Clones

Figure 4:
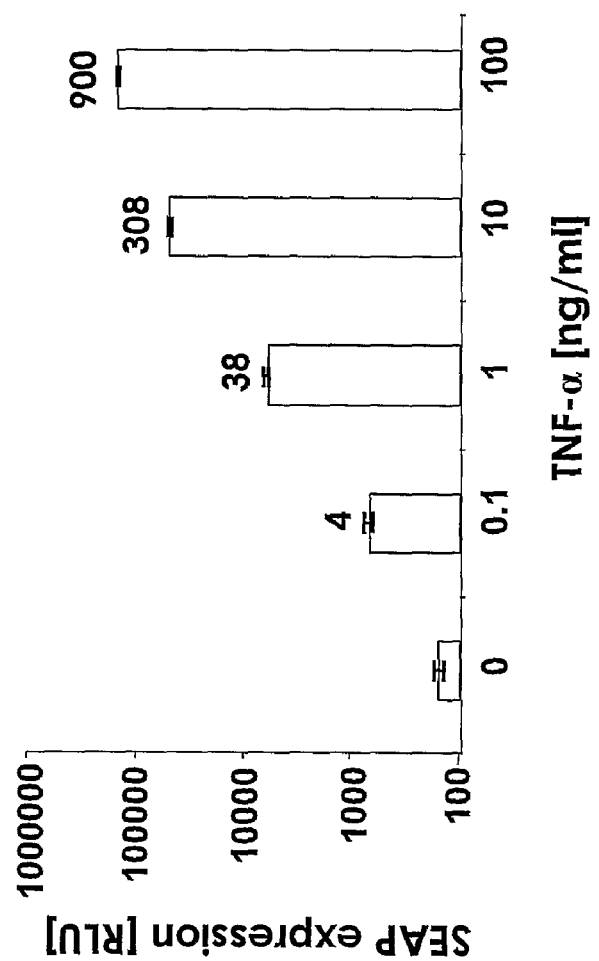
FIG. 4. SEAP activation in 24ST1NLESG cells at different concentrations of TNF-α. SEAP synthesis by 24ST1NLESG cells ($10^6$/ml) four days post-activation with various concentrations (0.1 to 100 ng/ml) of TNF-α. The numbers above the bars show the fold induction of enzymatic activity calculated as ratio between the average value of RLU per sample induced cells compared to the mean RLU value of uninduced cells. RLU, relative light units. Results shown are the means and standard deviations of one of three representative experiments.

In order to provide a well characterized system to identify molecules that can activate latent virus, SupT1 cell clones harboring latent vector provirus were isolated. Cell clones were isolated by limiting dilution according to the standard protocol (11). Clones were then tested to determine if they harbored latent virus that could be stimulated with TNF-α. Flow cytometry to monitor GFP expression showed that after treatment with TNF-α there was a significant increase in the number of cells expressing GFP within each of the three clonal populations (FIG. 3A). All three lines also exhibited a significant fold induction in SEAP activity after treatment with TNF-α. By day 2 post treatment, SEAP activity increased by approximately 50-, 400-, and 150-fold in lines 19ST1NLESG, 24ST1NLESG, 29ST1NLESG, respectively (FIGS. 3B and C). The variation in the fold induction of the three cell clones was primarily due to differences between the background levels of expression (FIG. 3B). Given the relatively low background for 24ST1NLESG, and its high level of induction in SEAP activity reaching approximately 600-fold by day 4, attention was focused upon this cell line. To test the sensitivity and concentration dependence of the inducible 24ST1NLESG cell line, it was stimulated with various concentrations of TNF-α. Even at 0.1 ng/ml of TNF-α induction could be detected yielding SEAP activity 4-fold above background (FIG. 4).

Besides the two exogenous marker genes, seap and egfp, autologous HIV-1 gag gene expression can also be used as a marker for activation since the gag gene remains intact in the system. The Gag polyprotein is translated from full-length viral RNA, which is expressed during the late stage of viral infection. Monitoring of p24$^{gag}$, the viral capsid protein, could be useful for a secondary screen since there is a sensitive and straightforward ELISA available to measure its expression.

Figure 5:
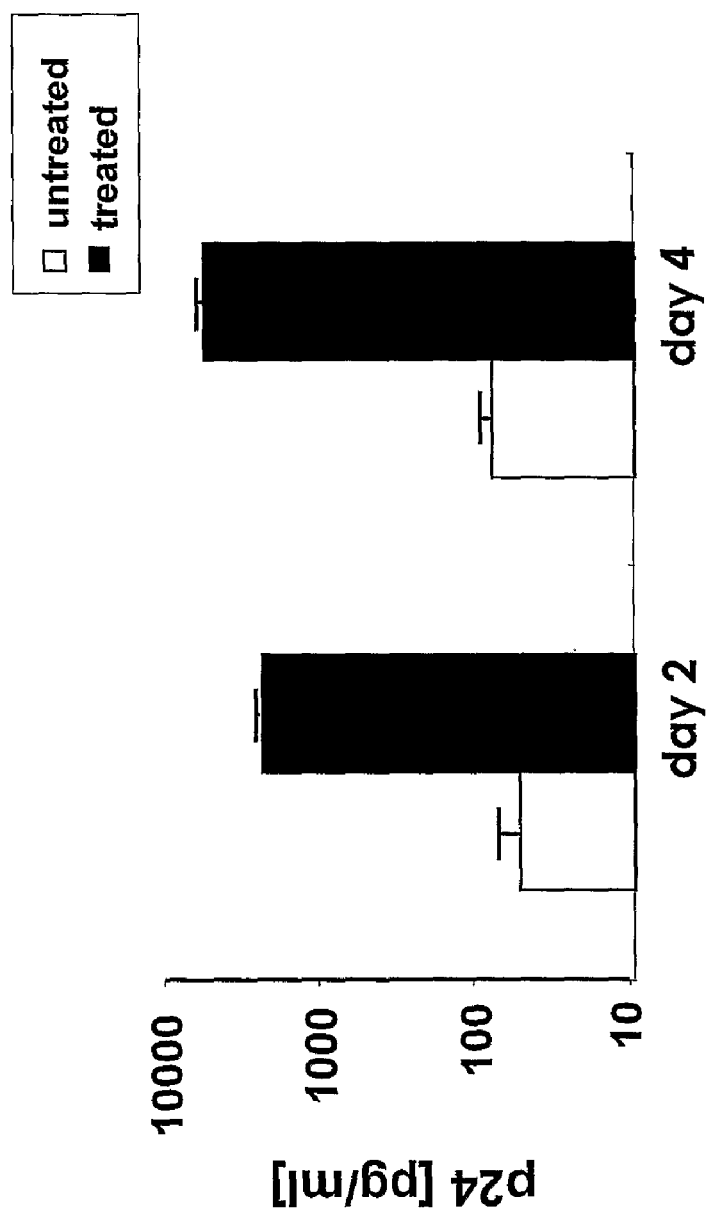
FIG. 5. HIV-1 Gag p24 protein production in 24ST1NLESG cells. HIV-1 Gag p24 protein was detected in the cultured media of untreated and TNF-α (50 ng/ml) treated 24ST1NLESG cells ($10^6$/ml) two and four days post-plating. Results shown are the means and standard deviations of one or two representative experiments.

To further characterize the 24ST1NLESG cell line, p24$^{gag}$ expression was monitored using the ELISA after treatment with TNF-α (50 ng/ml) (FIG. 5). As anticipated, the concentration of p24$^{gag}$ increased significantly at 2 and 4 days post-activation reaching levels 50 fold and 100-fold above background, respectively (FIG. 5).

The consistent reactivation of viral genes as evidenced by the pattern of expression of the three markers assayed correlated with an increase in the relative levels of total viral mRNA. The relative amount of total HIV-1 mRNA was determined by quantitative real-time PCR using primers to the second exon of rev (Rev2). Rev2 primers were chosen to amplify the viral transcripts since they are complimentary to sequences presented in all RNA species encoded by the provirus (38). RT PCR was primed with oligo d(T)16. Therefore, only the level of mature polyadenylated RNA was detected.

Figure 6:
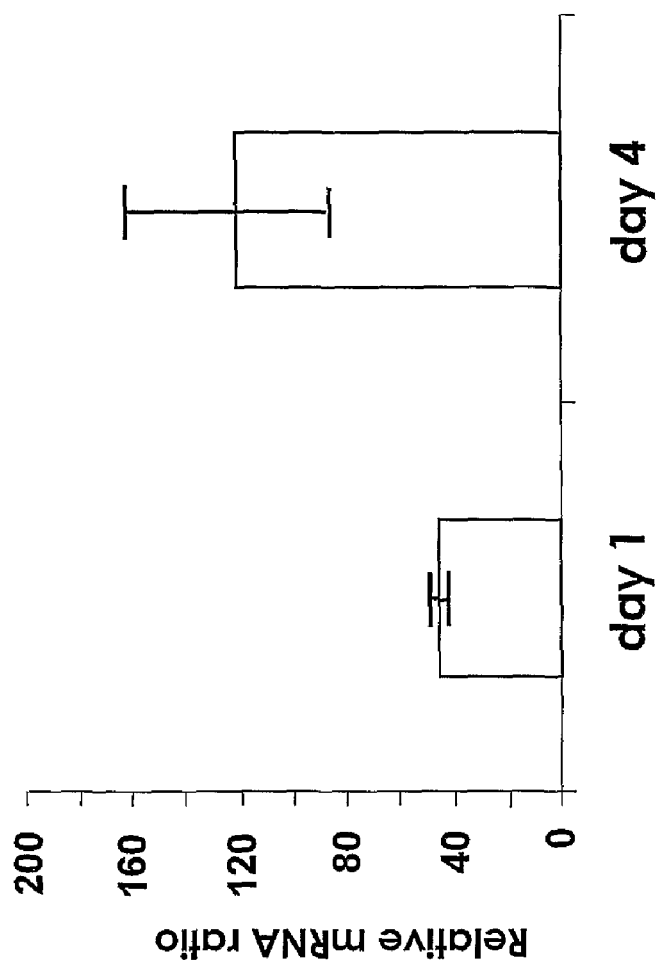
FIG. 6. Real-time RT-PCR for relative quantification of HIV-1 mRNA levels in 24ST1NLESG cells before and after activation from latency. Quantitative real-time RT-PCR was performed with RNA isolated from 24ST1NLESG cells ($10^6$/ml) following one and four days after stimulation with TNF-α (50 ng/ml). cDNA was synthesized with polyT oligo, and the reactions were completed with primers to viral (Rev2) and cellular (β-actin) genes with SYBR green detection. The 'Delta-delta method' (PE Applied Biosystems) was used to compare the relative expression results ($\Delta C_T$) between the values obtained from the RNA samples from stimulated cells to the values obtained from RNA isolated from untreated cells. The results were normalized to the expression of β-actin. The data are presented as the mean and standard deviation from two experiments.

The relative ratio of viral RNA after stimulation of 24ST1NLESG latent cells was determined as described in the Examples using the relative RNA results obtained for the unstimulated 24ST1NLESG cells as a control. β-actin was used as a reference gene. By day 4 post-stimulation with TNF-α (50 ng/ml), the relative ratio of viral RNA increased by at least 100-fold indicating that the increase in proviral protein expression resulted due to a significant increase in the steady-state levels of viral RNA (FIG. 6).

Figure 7:
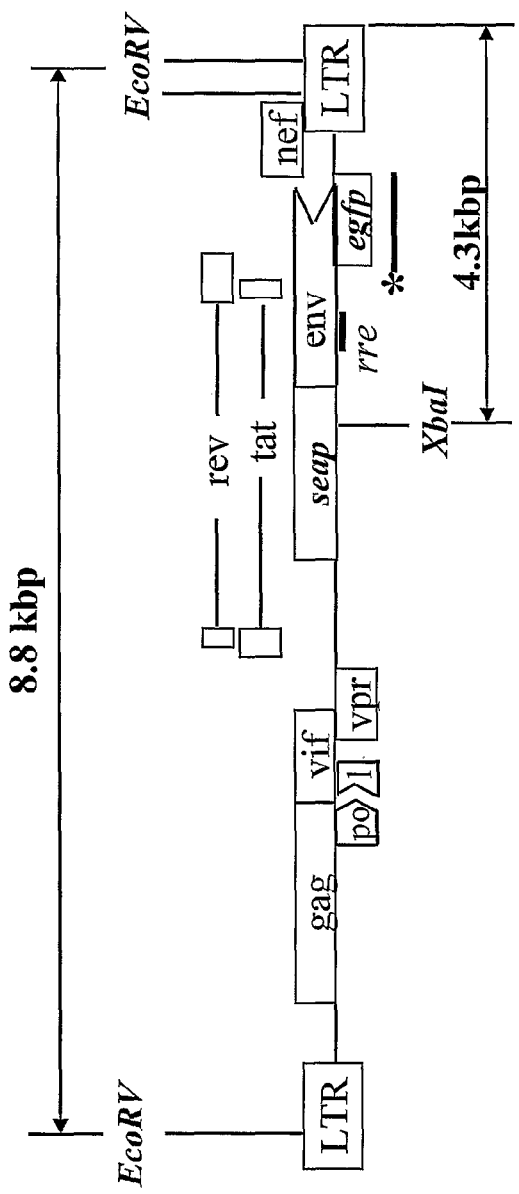
FIG. 7. Southern analysis to confirm clonality and the structure of the vector provirus. Genomic DNA samples from 19ST1NLESG, 24ST1NLESG, 29ST1NLESG cell clones, and parental SupT1 cells were digested with XbaI or EcoRV and subjected to Southern analysis. (A) Diagram of the viral vector NLE⁻S-G indicated the probe that is complimentary to the egfp gene and detects specific 8.8 kbp fragment from EcoRV digested proviruses. The distance from XbaI restriction site to the end of 3'LTR is illustrated. (B) Southern blot showing the 8.8 kbp diagnostic band resulting from EcoRV digestion in all three clones (lanes 7-9) and the fragments of various sizes generated by XbaI digestion due to the different site of provirus integration in the host genome (lanes 2-4). Lanes 1 and 6 are positive controls (+) and were loaded with 50 pg plasmid DNA digested with XbaI and EcoRV, respectively. Genomic DNA from parental cell line SupT1 was used as a carrier (lanes 1 and 6) or as a negative control (−) (lane 5).
Figure 7:
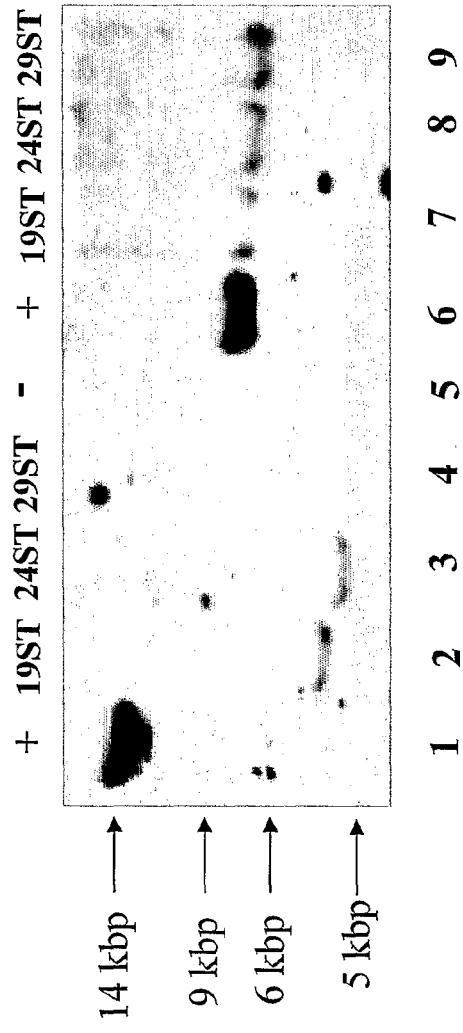

Southern blotting was performed to examine the proviral structure and the clonal nature of the cell lines. Genomic DNA was isolated from each of the cell clones followed by digestion with the EcoRV or XbaI and subsequent Southern analysis probing with egfp-specific sequence (FIG. 7). EcoRV cuts once within each LTR and would be expected to yield an 8.8 kbp band from each sample, which was the case (FIG. 7). XbaI cuts once within the provirus. Therefore, if each line represents a different cell clone, XbaI would be anticipated to yield a different size band because, given the random nature of proviral integration, the XbaI site in the adjacent genomic DNA will be in a different location. The XbaI digestion yielded bands of different size, between 5 and 6 kbp, indicating the three lines are different clones with disparate proviral integration sites (FIG. 7).

An advantage to using a defective HIV-1 provirus for monitoring proviral activation is that replication-competent virus is not produced, which is particularly important for HTS when a large number of samples are analyzed. However, it is prudent to test before wide-scale use of the system that RC virus was not produced during the development of the cell lines. To that end, the cell lines were analyzed for reverse transcriptase activity after treatment with 50 ng/ml of TNF-α. Since most of the pol gene was deleted from the vector, the cell lines should be negative for RT activity, which was the case (data not shown). Without RT activity, it should not be possible to passage RC virus. Nevertheless, the cell lines were tested further. As shown in FIG. 5, 24ST1NLESG cells produce HIV-1 capsid proteins. To prove that only defective virions were formed, an HIV-1 gag transfer assay was performed as described in the Examples. This test confirmed the lack of RC virus.

Assay Reliability

For the assay to be useful in a HTS it should be reliable in a small well format. Assay optimization and validation requires the determination of the Z' factor, a dimensionless statistical characteristic used to assess the quality of data generated in a potential HTS assay (48). It is a commonly used measure of assay performance and reliability that takes into account both the assay signal dynamic range (signal-to-background) and variation (signal-to-noise) associated with the measured signals.

The Z' factor values for the latency assay of the present invention were calculated based on the analysis of SEAP expression from uninduced (negative) and induced (positive) 24ST1NLESG cells. Eighty-eight wells of a 96-well plate were seeded with $10^5$ cells/well either in media alone or media containing an inducer in a final volume of 20 μl. The remaining 8 wells contained serial dilutions of SEAP protein as a positive control for the assay. The plates were assayed for the presence of SEAP after 48 hours. The readouts for each plate were compiled and the Z' factor for each inducer and the uninduced control was determined using the equation:

$$Z' = 1 - \frac{(3\sigma_{positive} + 3\sigma_{negative})}{|\mu_{positive} - \mu_{negative}|}$$

where σ represents the standard deviation and μ is the mean of each set of data points. A perfect assay would have a Z' factor value of 1, while an excellent assay would score between 0.5 and 1. If the Z' value falls between 0 and 0.5, the performance of the assay should be improved. Any score ≦0 is indicative of an insignificant separation between the background and the positive signal and the assay must therefore be redesigned (47). Since the Z' factor is dimensionless, the reliability of assays performed separately but which are similar in design may be directly compared.

Figure 8:
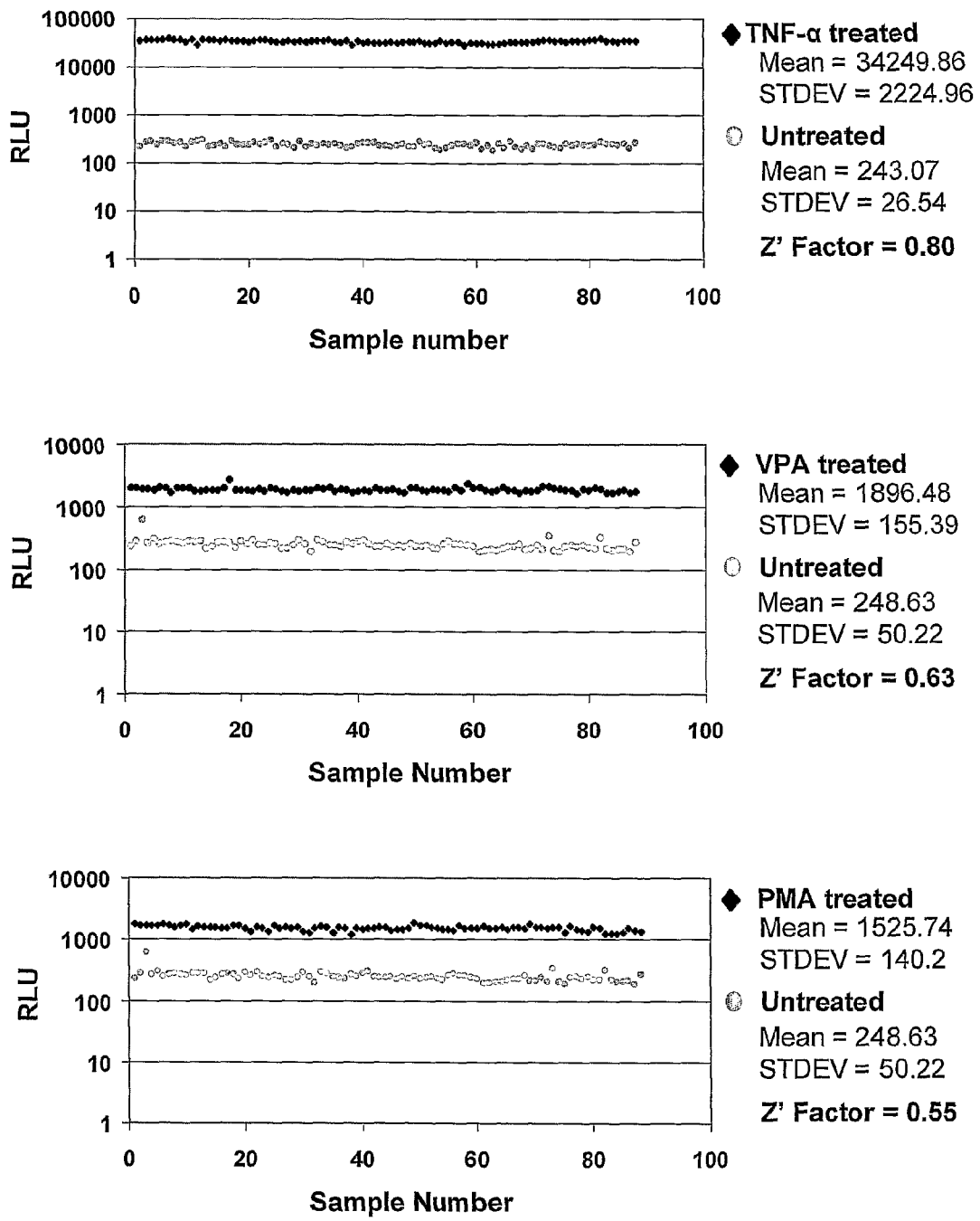
FIG. 8. Z' Factor Determination. 24ST1NLESG ($10^5$/well) cells were seeded in 96-well plates and both uninduced, (●) and induced (◆) cells were assayed for SEAP activity after 48 h. Cells were treated with 50 ng/ml TNF-α (A), 1 mM valporic acid (VPA) (B), and 100 ng/ml PMA (C). The results from 88 samples per plate were compiled and the Z' factor was determined using the formula given in the section entitled assay reliability.

The Z' factors for the latency assay with 24ST1NLESG cells of the present invention are shown in FIG. 8. Induction with 50 ng/ml TNF-α in a 96-well format resulted in a Z' factor of 0.8, while activation with 1 mM VPA and 100 ng/ml PMA returned Z' scores of 0.63 and 0.55, respectively. A certain amount of variability in these assays was expected since pipetting by hand during seeding and performance of the SEAP detection assay can introduce some variation. Even with this inherent variability, the Z' values for all three tested compounds are above 0.5, indicating excellent assay performance.

EXAMPLES

Example 1

Packaging and Transducing Vectors

The recombinant transducing vector used in this study was based on the NL4-3 hemigenomic plasmid. A 2.5 kb deletion in the pol gene was made by splicing by overlap extension (25). Three PCR products were generated: (i) sequence between the unique BssHII site (coordinate 710) and the stop codon of gag at 2300, (ii) sequence stretching from 100 bp upstream of the start codon of vif (coordinate 4840) to the unique EcoRI site (coordinate 5744), (iii) a 2.5 kb product formed by linking products i and ii by PCR sequence overlap extension (SOE). The PCR product (iii) containing the deleted pol gene was cloned into pGEM (Promega) and was excised from there with BssHII and EcoRI followed by ligation into the BssHII/EcoRI digested NL4-3 backbone yielding pNL2.5p$^-$. The same method was used to insert the egfp coding sequence 10 bp upstream from the start codon of nef while deleting 80 bp from the 3' of env: coordinates 8700 to 8780. Five PCR products also were made: (a) from the unique BamHI site (coordinate 8465) in env to 50 bp downstream of the stop codon of rev (coordinate 8680), (b) the egfp gene including the Kozak sequence (30), (c) products a and b linked by SOE PCR, (d) from the start codon of nef to the unique XhoI site in nef, (e) products c and d linked by SOE PCR. Product e was cloned into pGEM and cut from there with BamHI and XhoI. The BamHI-XhoI fragment was ligated into the pNL2.5p$^-$ backbone, which was digested with BamHI and XhoI to obtain the NLp$^-$e$^+$G construct.

The start codons of vpu and env were altered by site-directed mutagenesis (Stratagene). The NL4-3 genome from EcoRI to NheI (1.5 bp) was subcloned into a modified pSEAP-Basic vector, where BamHI-BamHI deletion of the SEAP gene was made, and the ClaI restriction site was created in place of the start codon of env (e*).

The SEAP open reading frame was cut from pSEAP-Basic (CLONTECH Laboratories) with ClaI and BsmI and ligated into plasmid NLp$^-$e*G linearized with ClaI. The in-frame orientation of SEAP was confirmed with restriction enzyme digestion and DNA sequencing. Thus pNLE$^-$S-G (FIG. 1A) was created.

pCMVΔR8.2, a CMV promoter-driven HIV packaging plasmid with all accessory proteins, was used to compensate for the lack of pol gene expression. pMD.G was used to provide expression of vesicular stomatitis virus G env (VSV-G)(33).

Example 2

Cell Culture and Reagents 293T cells were grown in minimal essential medium (MEM) supplemented with 10% fetal bovine serum (Hyclone), 0.2 mM MEM non-essential amino acid solution (GIBCO BRL 11095-080), 250 U/ml penicillin, and 250 μg/ml streptomycin (GIBCO BRL 11140-050). SupT1 cells as well as 19ST1NLESG, 24ST1NLESG, and 29ST1NLESG cells were maintained in RPMI 1640 medium supplemented with 10% fetal bovine serum and 2 mM L-glutamine. TNF-α was obtained from R&D Systems (Minneapolis, Minn.). PMA, and valporic acid, were purchased from Sigma (St. Louis, Mo.).

Example 3

Virus Production, Infection and Isolation of Latent Clones

Vector virus was produced using transient, three-plasmid co-transfection via modified calcium phosphate precipitation method (21). Twenty-four hours after plating, 293T cells ($2.5 \times 10^6$ per 100-mm-diameter dish) were co-transfected with pNLE$^-$S-G (5 μg), pCMVΔR8.2 (5 μg), and pMD.G (4 μg). Viral supernatant was collected from 20 plates 48 h post-transfection and was concentrated by ultracentrifugation for 1.5 h at 50,000 g in a Beckman 45 Ti rotor at 4° C. Viral particles were resuspended in 2 ml media with 8 μg/ml polybrene and the viral concentrate was used to infect $5 \times 10^6$ SupT1 cells. The inoculation was preceded by spinoculation (34) at 1,200 g for 2 h at 25° C. After 6 h of incubation at 37° C. and 5% CO2, SupT1 cells were washed twice with PBS and resuspended in fresh media. Four weeks post-infection, the mass population of SupT1 infected cells was used to isolate clones harboring latent provirus. This was done by limiting dilution following the standard protocol (11). Only the clones that showed significant increase of SEAP activity after activation with 100 ng/ml TNF-α were chosen.

Example 4

Assays for Replication-Competent Virus

HIV gag transfer assay. $1 \times 10^6$ SupT1 infected cells (latent mass population and clonal cell lines) were plated followed by harvesting supernatant one week later. Samples were collected both from TNF-α activated and untreated cells. They were passed through a 0.45-μm pore-size filter and used to inoculate $2 \times 10^6$ parental SupT1 cells for 24 h. The cells were washed twice with PBS and resuspended in fresh media. The same process was repeated once again with conditioned media from the targeted parental cells, and a new batch of SupT1 cells was treated. Passing the conditioned media over two sets of virgin SupT1 cells helps to assure that the carryover of gag protein in the samples will be eliminated and only the de novo synthesized protein, if present, will be assessed. Samples harvested after one week post-incubation were used to determine the concentration of p24 using an HIV-1 p24$^{gag}$ ELISA kit according to the manufacturer's protocol (Perkin Elmer Life Sciences). Samples were considered virus free when the p24$^{gag}$ concentration was below the detection threshold, which for this assay, was determined to be 10 pg/ml.

Reverse transcriptase assay. Four days after plating the conditioned media from the clonal latent cell lines (both TNF-α stimulated and untreated) was used to determine the activity of HIV-1 RT using a calorimetric enzyme immunoassay (Roche Applied Sciences). The sensitivity threshold for this assay is 1 pg per reaction or 50 pg/ml. The detection limit according to the manufacturer's protocol was defined to be a signal level of twice the background, which in our assay was represented by conditioned media from untreated parental SupT1 cells.

Example 5

Flow Cytometric Analysis

Flow cytometric analysis was performed with a FACScan (Beckman-Coulter) using CellQuest software. Prior to the flow cytometric analysis 1×10⁶ cells were washed twice and resuspended in 1 ml of PBS.

Example 6

Southern Blotting

Isolation of genomic DNA and Southern blotting analysis were done according to standard procedures (1). Genomic DNA (20 µg) was digested with EcoRV or XbaI and electrophoresed on a 0.8% agarose gel. Blots were then hybridized with $^{32}$P-labeled probe complimentary to egfp sequence in the pNLE⁻S-G transducing vector.

Example 7

SEAP Assay for Detection of Late Gene Expression

1×10⁶ or 1×10⁵ cells from the clonal cell lines or mass populations of infected cells were resuspended in RPMI media with or without the activator. At the indicated day post plating, samples were taken to determine the activity of SEAP. The assay was performed using a SEAP Detection kit (BD Biosciences, Palo Alto, Calif.) according to the manufacturer's protocol. The relative light units (RLU) were measured with a tube luminometer (Turner Designs 20/20) or a MLX Microtiter Plate Luminometer (DYNEX Technologies).

Example 8

Quantitative Real-Time RT-PCR

Total cellular RNA was isolated from untreated or TNF-α (50 ng/ml) stimulated 24ST1NLESG (1×10⁶) cells using the RNeasy Mini Kit according to the manufacturer's instructions (QIAGEN, Maryland, USA). Extracted RNA was subsequently treated with RQ1 DNase Kit (Promega, Madison Wis., USA) to remove the traces of DNA. The removal of DNA was confirmed with real-time PCR as described below by the lack of detectable signal above background amplification observed in the no-template reactions. Two-step real-time PCR was performed for relative quantification of viral RNA. cDNA was synthesized with TaqMan reverse transcription reagents and oligo d(T)16 following the protocol supplied by Applied Biosystems (Roche N.J., USA).

For each experiment, cDNA was synthesized with 5 µg of DNase treated RNA in 50 µl reaction volumes incubated at 25° C., 10 min; 48° C., 30 min, and 95° C., 5 min. Real-time PCR was accomplished with SYBR Green PCR Master Mix and run in DNA Engine Opticon 2 (MJ Research) detector with Opticon Monitor Analysis software version 1.4. Reactions received 5 µl of cDNA and 2.5 µM of each primer in a 25 µl reaction volume. The primer pair sequences used in the reactions are as follows:

forward 5'-CTGGAACGGTGAAGGTGACA-3' (SEQ ID NO:1), and
reverse 5'-AAGGGACTTCCTGTAACAATGCA-3' (SEQ ID NO:2) for β-actin;
forward 5'-AGGTGGAGAGAGAGACAGAGACA-3' (SEQ ID NO:3), and
reverse 5'-TCCCAGAAGTTCCACAATCC-3' (SEQ ID NO:4) for Rev2. Real-time PCR was carried out with a single thermocycle protocol of 95° C., 3 min; and 41 cycles of 95° C., 20 s, followed by 55° C., 1 min.

For each primer set, amplification efficiencies were determined by obtaining a standard curve with serial dilutions of cDNA from stimulated cells; the log of the relative target quantity was plotted against the CT (cycle threshold) value. The standard curves with slopes −5.53 and −5.13 showed amplification efficiencies 98 and 99% for β-actin and Rev2 primer pairs, respectively. A dissociation curve was generated for each primer pair and demonstrated the amplification of a single product. The sizes of the amplified products were confirmed by agarose gel electrophoresis and the specificity of the products was confirmed by sequencing. Reactions were completed in duplicate and no-template no-reverse transcriptase controls were included per primer pair. Relative RNA abundance ΔCT per sample was determined as the difference between the target gene CT value and the CT observed for the reference gene. The relative expression ratio was calculated using the formula $2^{-\Delta\Delta Ct}$ ('Delta-delta method' PE Applied Biosystems), where ΔΔCt is the difference between the relative RNA abundance in the sample in question and the control sample. The ΔCT of the untreated 24ST1NLESG cells was used as a control to the relative RNA abundance in TNF-α stimulated cells.

REFERENCES

1. Ausubel, F. M., R. Brent, R. E. Kingston, D. D. Moore, J. G. Seidman, J. A. Smith, and K. Struhl. 1994. Current Protocols in Molecular Biology. John Wiley & Sons, Inc., Hoboken, N.J.
2. Berger, J., J. Hauber, R. Hauber, R. Geiger, and B. R. Cullen. 1988. Secreted placental alkaline phosphatase: a powerful new quantitative indicator of gene expression in eukaryotic cells. Gene 66: 1-10.
3. Blankson, J. N., D. Persaud, and R. F. Siliciano. 2002. The challenge of viral reservoirs in HIV-1 infection. Annu. Rev. Med. 53:557-593.
4. Brinkman, K., J. A. Smeitink, J. A. Romijn, and P. Reiss. 1999. Mitochondrial toxicity induced by nucleoside-analogue reverse-transcriptase inhibitors is a key factor in the pathogenesis of antiretroviral-therapy-related lipodystrophy. Lancet 354:1112-1115.
5. Brooks, D. G., P. A. Arlen, L. Gao, C. M. Kitchen, and J. A. Zack. 2003. Identification of T cell-signaling pathways that stimulate latent HIV in primary cells. Proc. Natl. Acad. Sci. U.S.A 100:12955-12960.
6. Burns, J. C., T. Friedmann, W. Driever, M. Burrascano, and J. K. Yee. 1993. Vesicular stomatitis virus G glycoprotein pseudotyped retroviral vectors: concentration to very high titer and efficient gene transfer into mammalian and non-mammalian cells. Proc Natl Acad Sci USA 90:8033-8037.
7. Chun, T. W., R. T. Davey, Jr., M. Ostrowski, J. J. Shawn, D. Engel, J. I. Mullins, and A. S. Fauci. 2000. Relationship between pre-existing viral reservoirs and the re-emergence of plasma viremia after discontinuation of highly active anti-retroviral therapy. Nat. Med. 6:757-761.
8. Chun, T. W., D. Engel, S. B. Mizell, C. W. Hallahan, M. Fischette, S. Park, R. T. Davey, Jr., M. Dybul, J. A. Kovacs, J. A. Metcalf, J. M. Mican, M. M. Berrey, L. Corey, H. C. Lane, and A. S. Fauci. 1999. Effect of interleukin-2 on the pool of latently infected, resting CD4+ T cells in HIV-1-infected patients receiving highly active anti-retroviral therapy. Nat. Med. 5:651-655.
9. Chun, T. W., J. S. Justement, R. A. Lempicki, J. Yang, G. Dennis, Jr., C. W. Hallahan, C. Sanford, P. Pandya, S. Liu, M. McLaughlin, L. A. Ehler, S. Moir, and A. S. Fauci. 2003. Gene expression and viral production in latently infected, resting CD4+ T cells in viremic versus aviremic HIV-infected individuals. Proc. Natl. Acad. Sci. U.S.A 100:1908-1913.
10. Chun, T. W., L. Stuyver, S. B. Mizell, L. A. Ehler, J. A. Mican, M. Baseler, A. L. Lloyd, M. A. Nowak, and A. S. Fauci. 1997. Presence of an inducible HIV-1 latent reservoir during highly active antiretroviral therapy. Proc. Natl. Acad. Sci. U.S.A 94:13193-13197.
11. Coligan, J., A. Kruisbeek, D. Margulies, E. Shevach, and Strober. W. 1991. Current Protocols in Immunology. Green Publishing Associates and Wiley-Enterscience.
12. Davey, R. T., Jr., N. Bhat, C. Yoder, T. W. Chun, J. A. Metcalf, R. Dewar, V. Natarajan, R. A. Lempicki, J. W. Adelsberger, K. D. Miller, J. A. Kovacs, M. A. Polis, R. E. Walker, J. Falloon, H. Masur, D. Gee, M. Baseler, D. S. Dimitrov, A. S. Fauci, and H. C. Lane. 1999. HIV-1 and T cell dynamics after interruption of highly active antiretroviral therapy (HAART) in patients with a history of sustained viral suppression. Proc. Natl. Acad. Sci. U.S.A 96:15109-15114.
13. Dybul, M., B. Hidalgo, T. W. Chun, M. Belson, S. A. Migueles, J. S. Justement, B. Herpin, C. Perry, C. W. Hallahan, R. T. Davey, J. A. Metcalf, M. Connors, and A. S. Fauci. 2002. Pilot study of the effects of intermittent interleukin-2 on human immunodeficiency virus (HIV)-specific immune responses in patients treated during recently acquired HIV infection. J. Infect. Dis. 185:61-68.
14. Elgin, S. C. and S. I. Grewal. 2003. Heterochromatin: silence is golden. Curr. Biol. 13:R895-R898.
15. Finzi, D., J. Blankson, J. D. Siliciano, J. B. Margolick, K. Chadwick, T. Pierson, K. Smith, J. Lisziewicz, F. Lori, C. Flexner, T. C. Quinn, R. E. Chaisson, E. Rosenberg, B. Walker, S. Gange, J. Gallant, and R. F. Siliciano. 1999. Latent infection of CD4+ T cells provides a mechanism for lifelong persistence of HIV-1, even in patients on effective combination therapy. Nat. Med. 5:512-517.
16. Finzi, D., M. Hermankova, T. Pierson, L. M. Carruth, C. Buck, R. E. Chaisson, T. C. Quinn, K. Chadwick, J. Margolick, R. Brookmeyer, J. Gallant, M. Markowitz, D. D. Ho, D. D. Richman, and R. F. Siliciano. 1997. Identification of a reservoir for HIV-1 in patients on highly active antiretroviral therapy. Science 278:1295-1300.
17. Folks, T., D. M. Powell, M. M. Lightfoote, S. Benn, M. A. Martin, and A. S. Fauci. 1986. Induction of HTLV-III/LAV from a nonvirus-producing T-cell line: implications for latency. Science 231:600-602.
18. Folks, T. M., K. A. Clouse, J. Justement, A. Rabson, E. Duh, J. H. Kehrl, and A. S. Fauci. 1989. Tumor necrosis factor alpha induces expression of human immunodeficiency virus in a chronically infected T-cell clone. Proc. Natl. Acad. Sci. U.S.A 86:2365-2368.
19. Fondere, J. M., G. Petitjean, M. F. Huguet, S. L. Salhi, V. Baillat, A. ura-Biegun, P. Becquart, J. Reynes, and J. P. Vendrell. 2004. Human immunodeficiency virus type 1 (HIV-1) antigen secretion by latently infected resting CD4+ T lymphocytes from HIV-1-infected individuals. J. Virol. 78:10536-10542.
20. Furtado, M. R., R. Balachandran, P. Gupta, and S. M. Wolinsky. 1991. Analysis of alternatively spliced human immunodeficiency virus type-1 mRNA species, one of which encodes a novel tat-env fusion protein. Virology 185:258-270.
21. Gorman, C. 1985. High efficiency gene transfer into mammalian cells, p. 143-190. In: D. M. Glover (ed.), DNA Cloning. IRL Press, Oxford.
22. Han, Y., K. Lassen, D. Monie, A. R. Sedaghat, S. Shimoji, X. Liu, T. C. Pierson, J. B. Margolick, R. F. Siliciano, and J. D. Siliciano. 2004. Resting CD4+ T cells from human immunodeficiency virus type 1 (HIV-1)-infected individuals carry integrated HIV-1 genomes within actively transcribed host genes. J. Virol. 78:6122-6133.
23. He, G. and D. M. Margolis. 2002. Counterregulation of chromatin deacetylation and histone deacetylase occupancy at the integrated promoter of human immunodeficiency virus type 1 (HIV-1) by the HIV-1 repressor YY1 and HIV-1 activator Tat. Mol. Cell Biol. 22:2965-2973.
24. Hermankova, M., J. D. Siliciano, Y. Zhou, D. Monie, K. Chadwick, J. B. Margolick, T. C. Quinn, and R. F. Siliciano. 2003. Analysis of human immunodeficiency virus type 1 gene expression in latently infected resting CD4+ T lymphocytes in vivo. J Virol 77:7383-7392.
25. Ho, S. N., H. D. Hunt, R. M. Horton, J. K. Pullen, and L. R. Pease. 1989. Site-directed mutagenesis by overlap extension using the polymerase chain reaction. Gene 77:51-59.
26. Jordan, A., P. Defechereux, and E. Verdin. 2001. The site of HIV-1 integration in the human genome determines basal transcriptional activity and response to Tat transactivation. EMBO J. 20:1726-1738.
27. Korin, Y. D., D. G. Brooks, S. Brown, A. Korotzer, and J. A. Zack. 2002. Effects of prostratin on T-cell activation and human immunodeficiency virus latency. J Virol 76:8118-8123.
28. Kulkosky, J., D. M. Culnan, J. Roman, G. Dornadula, M. Schnell, M. R. Boyd, and R. J. Pomerantz. 2001. Prostratin: activation of latent HIV-1 expression suggests a potential inductive adjuvant therapy for HAART. Blood 98:3006-3015.
29. Kulkosky, J., J. Sullivan, Y. Xu, E. Souder, D. H. Hamer, and R. J. Pomerantz. 2004. Expression of latent HAART-persistent HIV type 1 induced by novel cellular activating agents. AIDS Res. Hum. Retroviruses 20:497-505.
30. Kutsch, O., E. N. Benveniste, G. M. Shaw, and D. N. Levy. 2002. Direct and quantitative single-cell analysis of human immunodeficiency virus type 1 reactivation from latency. J Virol 76:8776-8786.
31. Lafeuillade, A., C. Poggi, S. Chadapaud, G. Hittinger, M. Chouraqui, M. Pisapia, and E. Delbeke. 2001. Pilot study of a combination of highly active antiretroviral therapy and cytokines to induce HIV-1 remission. J. Acquir. Immune. Defic. Syndr. 26:44-55.
32. Lassen, K. G., J. R. Bailey, and R. F. Siliciano. 2004. Analysis of human immunodeficiency virus type 1 transcriptional elongation in resting CD4+ T cells in vivo. J. Virol. 78:9105-9114.
33. Naldini, L., U. Blomer, P. Gallay, D. Ory, R. Mulligan, F. H. Gage, I. M. Verma, and D. Trono. 1996. In vivo gene delivery and stable transduction of nondividing cells by a lentiviral vector. Science 272:263-267.

34. O'Doherty, U., W. J. Swiggard, and M. H. Malim. 2000. Human immunodeficiency virus type 1 spinoculation enhances infection through virus binding. J. Virol. 74:10074-10080.
35. Pacchia, A. L., M. E. Adelson, M. Kaul, Y. Ron, and J. P. Dougherty. 2001. An inducible packaging cell system for safe, efficient lentiviral vector production in the absence of HIV-1 accessory proteins. Virology 282:77-86.
36. Perelson, A. S., P. Essunger, Y. Cao, M. Vesanen, A. Hurley, K. Saksela, M. Markowitz, and D. D. Ho. 1997. Decay characteristics of HIV-1-infected compartments during combination therapy. Nature 387:188-191.
37. Prins, J. M., S. Jurriaans, R. M. van Praag, H. Blaak, R. van Rij, P. T. Schellekens, I. J. ten Berge, S. L. Yong, C. H. Fox, M. T. Roos, F. de Wolf, J. Goudsmit, H. Schuitemaker, and J. M. Lange. 1999. Immuno-activation with anti-CD3 and recombinant human IL-2 in HIV-1-infected patients on potent antiretroviral therapy. AIDS 13:2405-2410.
38. Purcell, D. F. and M. A. Martin. 1993. Alternative splicing of human immunodeficiency virus type 1 mRNA modulates viral protein expression, replication, and infectivity. J. Virol. 67:6365-6378.
39. Roberts, B. D., G. Fang, and S. T. Butera. 1997. Influence of cell cycle on HIV-1 expression differs among various models of chronic infection. Arch. Virol. 142:1087-1099.
40. Schwartz, S., B. K. Felber, D. M. Benko, E. M. Fenyo, and G. N. Pavlakis. 1990. Cloning and functional analysis of multiply spliced mRNA species of human immunodeficiency virus type 1. J Virol 64:2519-2529.
41. Stellbrink, H. J., F. T. Hufert, K. Tenner-Racz, J. Lauer, C. Schneider, H. Albrecht, P. Racz, and J. van Lunzen. 1998. Kinetics of productive and latent HIV infection in lymphatic tissue and peripheral blood during triple-drug combination therapy with or without additional interleukin-2. Antivir. Ther. 3:209-214.
42. Wang, F. X., Y. Xu, J. Sullivan, E. Souder, E. G. Argyris, E. A. Acheampong, J. Fisher, M. Sierra, M. M. Thomson, R. Najera, I. Frank, J. Kulkosky, R. J. Pomerantz, and G. Nunnari. 2005. IL-7 is a potent and proviral strain-specific inducer of latent HIV-1 cellular reservoirs of infected individuals on virally suppressive HAART. J. Clin. Invest 115:128-137.
43. Williams, S. A., L. F. Chen, H. Kwon, D. Fenard, D. Bisgrove, E. Verdin, and W. C. Greene. 2004. Prostratin antagonizes HIV latency by activating NF-kappaB. J. Biol. Chem. 279:42008-42017.
44. Winslow, B. J., R. J. Pomerantz, O. Bagasra, and D. Trono. 1993. HIV-1 latency due to the site of proviral integration. Virology 196:849-854.
45. Wong, J. K., M. Hezareh, H. F. Gunthard, D. V. Havlir, C. C. Ignacio, C. A. Spina, and D. D. Richman. 1997. Recovery of replication-competent HIV despite prolonged suppression of plasma viremia. Science 278:1291-1295.
46. Yang, T. T., P. Sinai, P. A. Kitts, and S. R. Kain. 1997. Quantification of gene expression with a secreted alkaline phosphatase reporter system. Biotechniques 23:1110-1114.
47. Zhang, J. and C. M. Sapp. 1999. Recombination between two identical sequences within the same retroviral RNA molecule. J. Virol. 73:5912-5917.
48. Zhang, J. H., T. D. Chung, and K. R. Oldenburg. 1999. A Simple Statistical Parameter for Use in Evaluation and Validation of High Throughput Screening Assays. J. Biomol. Screen. 4:67-73.

What is claimed is:

1. An in vitro, cell-based method of identifying compounds capable of activating latent HIV-1 comprising:

Providing an isolated SUPT1 cell line comprising a latent, HIV-1-derived provirus vector comprising:

An in-frame insertion of a secretable alkaline phosphatase (seap) gene open reading frame in place of the HIV-1 env gene start codon, an inactivation of the vpu gene start codon, a deletion of about 2500 base pairs of the HIV-1 pol gene, and an insertion of an egfp coding sequence 10 base pairs upstream from the nef gene start codon, wherein upon activation, the vector expresses the seap, a secretable marker for late viral gene expression, or the egfp, a marker for early viral gene expression;

providing a candidate compound and a positive control compound for late viral gene activation, wherein the positive control compound is selected from tumor necrosis factor-α, phorbol 12-myristate 13-acetate or valproic acid;

combining the cell line with the candidate compound and combining the cell line with the positive control compound;

monitoring for seap expression in the presence of the candidate compound as compared to seap expression in the absence of the candidate compound and monitoring for seap expression in the presence of the positive control to determine if the compound is capable of activating the vector late viral expression genes;

monitoring for egfp expression in the presence of the candidate compound as compared to egfp expression in the absence of the candidate compound and monitoring for egfp expression in the presence of the positive control to determine if the compound is capable of activating the vector early viral expression genes; and wherein detecting increased seap expression by monitoring an amount of seap expression that is greater in the presence of a candidate compound than in the absence of a candidate compound and/or detecting increased egfp expression by monitoring an amount of egfp expression that is greater in the presence of a candidate compound than in the absence of a candidate compound; and wherein detecting increased seap expression by monitoring an amount of seap expression that is greater in the presence of the positive control compound than in the absence of a the positive control compound and detecting increased egfp expression by monitoring an amount of egfp expression that is greater in the presence of the positive control compound than in the absence of the positive control compound, identifies a compound capable of activating latent HIV-1.

2. The method of claim 1, wherein the method further comprises detecting fluorescence by fluorescent microscopy, flow cytometry or combinations thereof.

3. The method of claim 1, wherein the provirus contains an intact HIV-1 Gag gene.

4. The method of claim 3, further comprising detecting HIV-1 Gag expression.

* * * * *

```
                        SEQUENCE LISTING

<160> NUMBER OF SEQ ID NOS: 4

<210> SEQ ID NO 1
<211> LENGTH: 20
<212> TYPE: DNA
<213> ORGANISM: Artificial Sequence
<220> FEATURE:
<223> OTHER INFORMATION: PCR Primer

<400> SEQUENCE: 1
ctggaacggt gaaggtgaca                                              20

<210> SEQ ID NO 2
<211> LENGTH: 23
<212> TYPE: DNA
<213> ORGANISM: Artificial Sequence
<220> FEATURE:
<223> OTHER INFORMATION: PCR Primer

<400> SEQUENCE: 2
aagggacttc ctgtaacaat gca                                          23

<210> SEQ ID NO 3
<211> LENGTH: 23
<212> TYPE: DNA
<213> ORGANISM: Artificial Sequence
<220> FEATURE:
<223> OTHER INFORMATION: PCR Primer

<400> SEQUENCE: 3
aggtggagag agagacagag aca                                          23
```

```
<210> SEQ ID NO 4
<211> LENGTH: 20
<212> TYPE: DNA
<213> ORGANISM: Artificial Sequence
<220> FEATURE:
<223> OTHER INFORMATION: PCR Primer

<400> SEQUENCE: 4
tcccagaagt tccacaatcc                                          20
```